United States Patent [19]
Peters

[11] Patent Number: 6,155,988
[45] Date of Patent: Dec. 5, 2000

[54] DEVICE FOR TAKING SAMPLES, FOR EXAMPLE FOR A BIOPSY, AND RACK SYSTEM FITTED TO SUCH A DEVICE

[75] Inventor: Jean-Bernard Peters, La Chaux-de-Fonds, Switzerland

[73] Assignee: Nivarox-FAR S.A., Le Locle, Switzerland

[21] Appl. No.: 09/272,163

[22] Filed: Mar. 19, 1999

[30] Foreign Application Priority Data

Mar. 26, 1998 [EP] European Pat. Off. ............. 98105473

[51] Int. Cl.⁷ ....................................................... A61B 5/00
[52] U.S. Cl. ............................................................ 600/564
[58] Field of Search ................................... 600/562, 564; 606/170, 174, 205–208

[56] References Cited

U.S. PATENT DOCUMENTS

| | | | |
|---|---|---|---|
| 5,201,759 | 4/1993 | Ferzli | 600/564 |
| 5,209,747 | 5/1993 | Knoepfler | 606/16 |
| 5,238,002 | 8/1993 | Devlin et al. | 128/751 |
| 5,275,615 | 1/1994 | Rose | 606/208 |
| 5,582,617 | 12/1996 | Klieman et al. | 606/170 |
| 5,683,413 | 11/1997 | Miyagi | 606/205 |
| 5,792,165 | 8/1998 | Klieman et al. | 606/170 |
| 5,817,119 | 10/1998 | Klieman et al. | 606/174 |
| 5,827,323 | 10/1998 | Klieman et al. | 606/205 |

FOREIGN PATENT DOCUMENTS 0 573 817 A1  5/1993  European Pat. Off. .
29 45 237 A1  5/1981  Germany .

*Primary Examiner*—Max Hindenburg
*Attorney, Agent, or Firm*—Pollock, Vande Sande & Amernick

[57] ABSTRACT

The present invention concerns a device for taking samples, for example for biopsies, of the type including a mechanical control system (2) sliding inside a flexible sheath (4) and connecting a control handle to a clamp (6) formed of pivoting jaws (8), characterised in that the control system (2) includes a cylindrical rack (28), and in that the jaws (8) of the clamp (6) each have, on a circular portion of their perimeter, a toothing (34) engaging the cylindrical rack (28) for the opening and closing of said jaws (8).

14 Claims, 5 Drawing Sheets

DEVICE FOR TAKING SAMPLES, FOR EXAMPLE FOR A BIOPSY, AND RACK SYSTEM FITTED TO SUCH A DEVICE

The present invention concerns a device for taking samples, for example for biopsies, of the type including a control cable sliding inside a flexible sheath, and a clamp formed of at least two pivoting jaws or grips. The invention also concerns a transmission rack system with improved mechanical couple between a driver pinion and a driven pinion.

Biopsy clamps are in particular used for taking tissue samples from the live organs of a patient, for example for the purposes of clinical tests. These clamps conventionally include cutting jaws actuated from a distance by a manipulator by means of a control device including a handle connected to the jaws by a cable system sliding inside a flexible sheath. The clamp and the flexible sheath are introduced into the tub of an endoscope via which the clamp is led to the desired location where the sample is to be taken.

This equipment is used by qualified personnel who, although warned of the fragility of these instruments, cannot avoid very frequent breakage of the cables which assure the opening and closing of the jaws of said instruments. It should be noted that these clamps, because of their destination and the manner in which they are used, are of very small dimensions and their cables are extremely thin. It should also be noted that the pressure which has to be exerted on the handle to assure the closing movement of the jaws must be strong enough to be able to remove fragments of tissue or mucous by cutting. This pressure cannot however be accurately measured and monitored, so that it is left to the person manipulating the device to evaluate the pressure which he does not always do correctly, which is the cause of cable breakage.

Various solutions have been proposed to attempt to overcome these problems and assure more accurate and efficient sample taking.

By way of example, U.S. Pat. No. 5,582,617 can be cited, which proposes a biopsy clamp of the type including two jaws articulated so as to pivot around a common axis, these jaws each having a circular toothed profile engaging a rectilinear rack crimp connected onto the control cable of the clamp. By traction on the cable, the clamp jaws close again.

Another embodiment of a clamp is known from U.S. Pat. No. 5,209,747. This clamp includes a control stem having two rectilinear racks which each engage the circular toothed profile of one of the jaws of the clamp.

These known solutions have several drawbacks. It will be noted first that the mechanical couple is transmitted to the jaws or driven pinions of the clamps by a single tooth of the rectilinear racks or driver pinions. The pressure exerted on the handle by the person manipulating the device is thus only partially transmitted to the jaws of the clamp, so that there is a significant risk of tearing and ripping the tissues to be taken. The fact that such clamps cannot include more than two jaws and that the volume of samples which they can take is therefore limited, should also be considered. Finally, such clamps are generally unreliable. In the event of breakage of the control cable or the crimp connection coming undone, there is a risk of the racks escaping and falling into the patient's body.

A biopsy clamp including a transmission cable sliding inside a flexible sheath and connecting a control handle to a clamp formed of two pivoting jaws is also known from U.S. Pat. No. 5,275,615. According to the biopsy clamp described in this document, the clamp includes a cylindrical control stem having two semi-circular racks which each engage the circular toothed profile of one of jaws of the clamp. Such a clamp cannot therefore include more than two jaws, which limits its sample taking volume. It will also be noted that the gearing used in this Patent is a standardized gearing with at least twelve apparent teeth distributed on the primitive diameter of the circular toothed profile of each of the jaws of the clamp. The drawbacks of standardized toothings are well known in the field of micro-mechanics: poor gearing guiding, fragile teeth, poor transmission of the mechanical couple exerted by the operator when he actuates the control handle.

The object of the present invention is to overcome the above problems and drawbacks by providing a device for taking samples, in particular for biopsies, which operates reliably and allows good transmission of the pressure exerted by the operator on the control handle to the clamp.

The invention therefore concerns a device for taking samples for example for biopsies, of the type including a mechanical control system sliding inside a flexible sheath and connecting a control handle to a clamp formed of pivoting jaws, characterised in that the control system includes a cylindrical rack, and in that the jaws of the clamp each have, on a circular portion of their perimeter, a toothing engaging the cylindrical rack for the opening and closing of said jaws.

Since the rack according to the invention has a general revolution symmetry, the number of jaws of the clamp can be increased and brought to at least three. It is thus possible to increase the sample volume of the clamp, and to improve the efficiency and accuracy of the sample taking.

According to another feature of the invention, the toothings of the jaws of the clamp engage the cylindrical rack with at least two of the teeth thereof. The mechanical couple corresponding to the pressure exerted by the operator on the control handle of the sample taking device according to the invention is thus transmitted in its entirety to the jaws of the clamp, which assure accurate and efficient sample taking, without risking tearing or ripping for example the tissues to be taken.

According to another feature of the invention, the toothings of the jaws of the clamp each have a stop which blocks the axial sliding of the cylindrical rack in an end of travel position. As a result of this other advantageous arrangement, the cylindrical rack cannot be lost even in the event of breakage of the control cable or release of the crimp connection or the welding, which provides a high level of security of use for the sample taking device according to the invention.

According to a further feature of the invention, the apparent number of teeth distributed on the primitive diameter of the gearing is at most six. Thus, by dividing the apparent number of teeth by two with respect to a standardized gearing, the present invention allows a gearing with more solid teeth, better guiding and better transmission of the mechanical couple exerted by the operator when he actuates the control handle, to be obtained.

The present invention also concerns a rack system including a driver pinion and a driven pinion, characterised in that the driver pinion is a cylindrical rack, and in that the driven pinion has, on a circular portion of the perimeter thereof, a toothing engaging the cylindrical rack.

Other features and advantages of the present invention will appear more clearly upon reading the following detailed description of an embodiment example of the sample taking device according to the invention, this example being given purely by way of illustrative and non limiting example, in conjunction with the annexed drawings, in which.

The sample taking device according to the invention will be described in the medical application thereof to the taking of tissue samples from live organs or biopsies. Nonetheless, it goes without saying that this device can be used for other purposes for gripping or taking samples, fragments or particles of various natures, organic, mineral or other.

Figure 1:
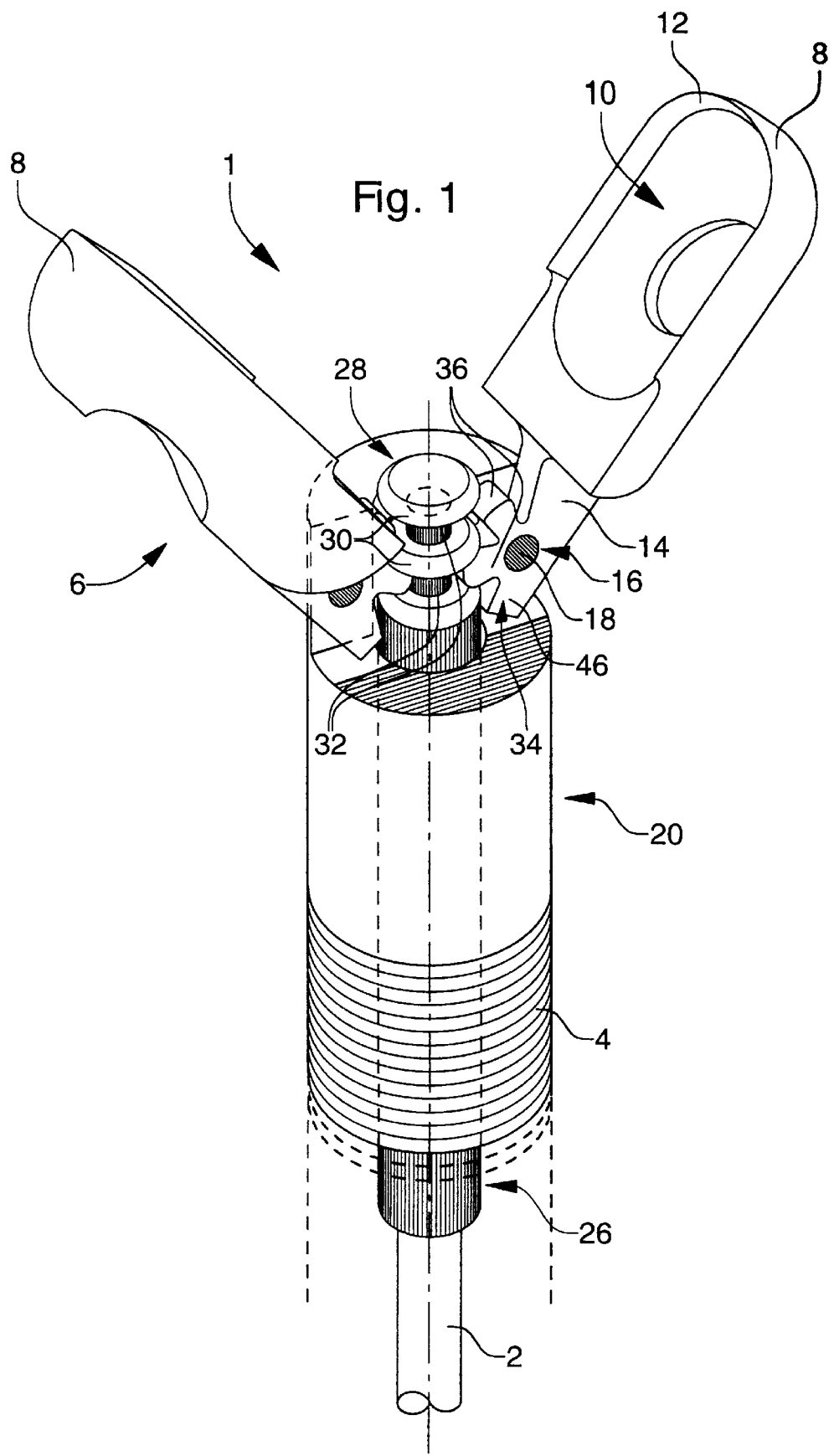
FIG. 1 is a general perspective view of the sampling clamp according to the invention in a fully open position with the fork partially torn away.

As FIG. 1 clearly shows, the sample taking device according to the invention, designated as a whole by the general numerical reference 1, includes a mechanical control system formed by a transmission cable 2 sliding axially inside a flexible sheath 4 and connecting a control handle (not shown) to a clamp 6 formed of two pivoting jaws 8. By traction on cable 2, jaws 8 of clamp 6 close.

Within the application of the present invention to forming biopsy clamps or other clamps intended to take samples of fragments of material, jaws 8 can have, on the inner face thereof, a substantially hemispherical cavity 10 having a cutting edge 12 towards its upper edge. Thus, when clamp 6 is closed, jaws 8 delimit a sufficiently significant sampling volume to encompass a fragment of biological tissue, a mineral or other fragment. Jaws 8 can be made entirely of stainless steel or of a suitable biocompatible plastic material, cutting edges 12 being then added onto jaws 8 in the form of metal inserts. It goes without saying that a significant range Of jaws 8 of different shapes can be proposed to users as a function of their requirements.

Figure 2:
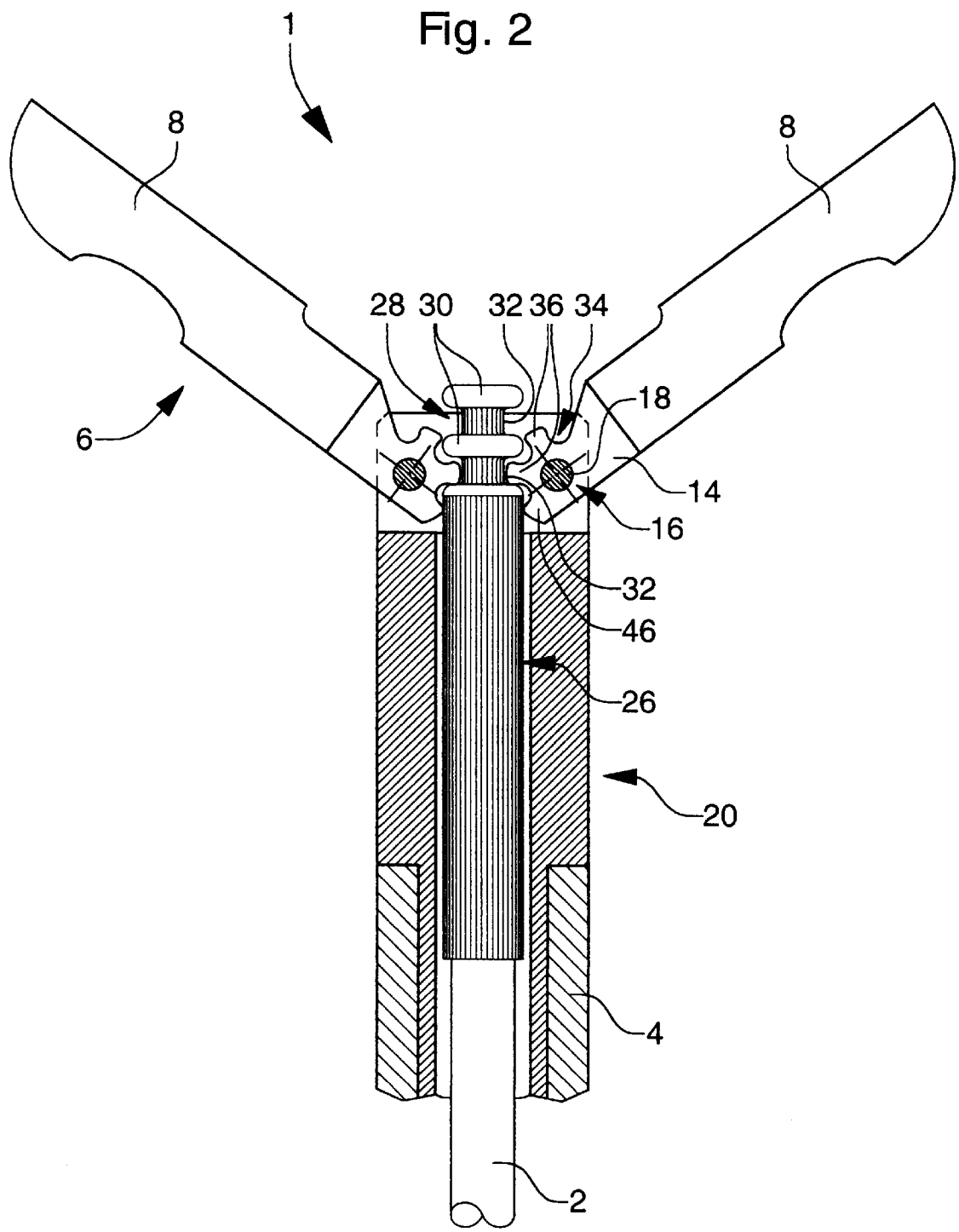
FIG. 2 is a longitudinal cross-section of the sampling clamp of FIG. 1 in a fully open position.
Figure 3:
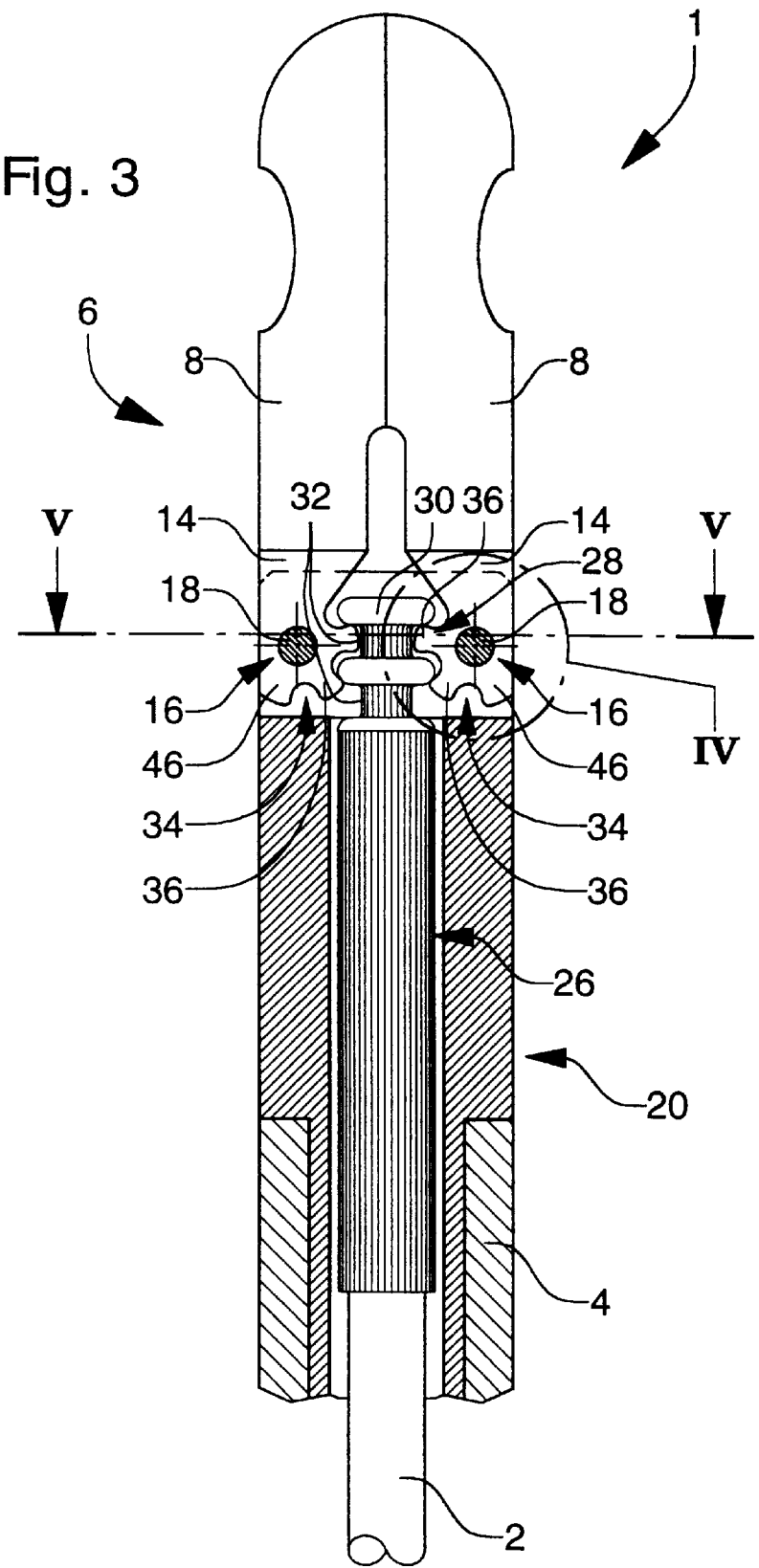
FIG. 3 is a longitudinal cross-section of the sampling clamp in a closed position.

Jaws 8 of clamp 6 each include a mounting branch 14 whose end has a hole 16 for the passage of a shaft 18. As FIG. 2 clearly shows, jaws 8 are mounted so as to pivot around shafts 18 on a fork 20 fixed to the distal end of flexible sheath 4 by crimp connection, welding or any other suitable technique. This fork 20, for example of generally cylindrical outer shape, has a diametrical groove 22 in which mounting branches 14 of jaws 8 are housed.

Jaws 8 of clamp 6 are thus completely protected and there is no risk of them being damaged during cleaning, conventionally by brushing, of said clamp 6.

According to the present invention, fork 20 also includes at the centre thereof a longitudinal channel 24 for guiding the axial sliding of a control stem 26 fixed by crimp connection, welding or other means to the free end of transmission cable 2. According to a first advantageous feature of the invention, control stem 26 has at the top thereof a cylindrical rack or driver pinion 28 formed by an alternating succession of annular teeth 30 and annular grooves 32. Teeth 30 which have the shape of full discs can advantageously be formed integral with control stem 26, for example by profile-turning. Cylindrical rack 28 shown in the Figures only includes two teeth 30. However, it goes without saying that as a function of the required destination and manner in which clamp 6 is to be used, this number can be increased.

Mounting branches 14 of jaws 8 each have on a circular portion of the perimeter thereof, a toothing or driven pinion 34 whose teeth 36 engage cylindrical rack 28 so that, by traction on transmission cable 2, jaws 8 of clamp 6 close.

Figure 4:
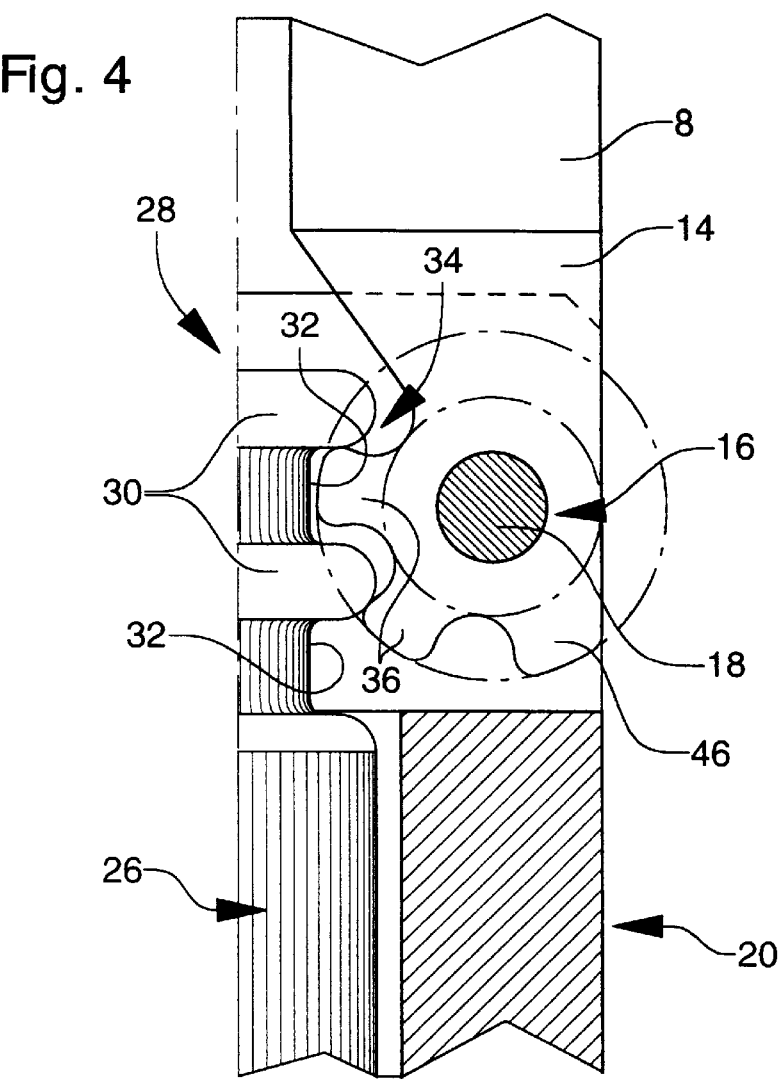
FIG. 4 is a detailed view of the portion surrounded with a dot and dash line in FIG. 3.
Figure 5:
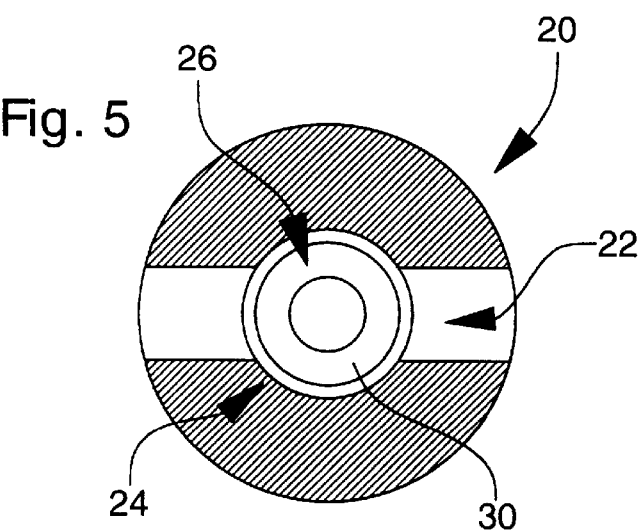
FIG. 5 is a cross-section along the line V—V of FIG. 3, the jaws of the clamp having been removed.

As FIG. 4 clearly shows, toothings or driven pinions 34 engage cylindrical rack or driver pinion 28 with two of their teeth 36. As a result of this feature, the mechanical couple corresponding to the pressure exerted by the operator on the control handle of the sample taking device according to the invention is transmitted in its entirety to jaws 8 of clamp 6, which assures accurate and efficient sample taking, without risking tearing or ripping the tissues to be taken. It should also be noted that the substantially revolution geometry of cylindrical rack 28 allows one to envisage increasing the number of jaws 8 which form clamp 6, bringing the number for example to three. It is thus possible to increase the sampling volume of clamp 6 and to further increase the accuracy and efficiency of the sample taking.

Figure 6:
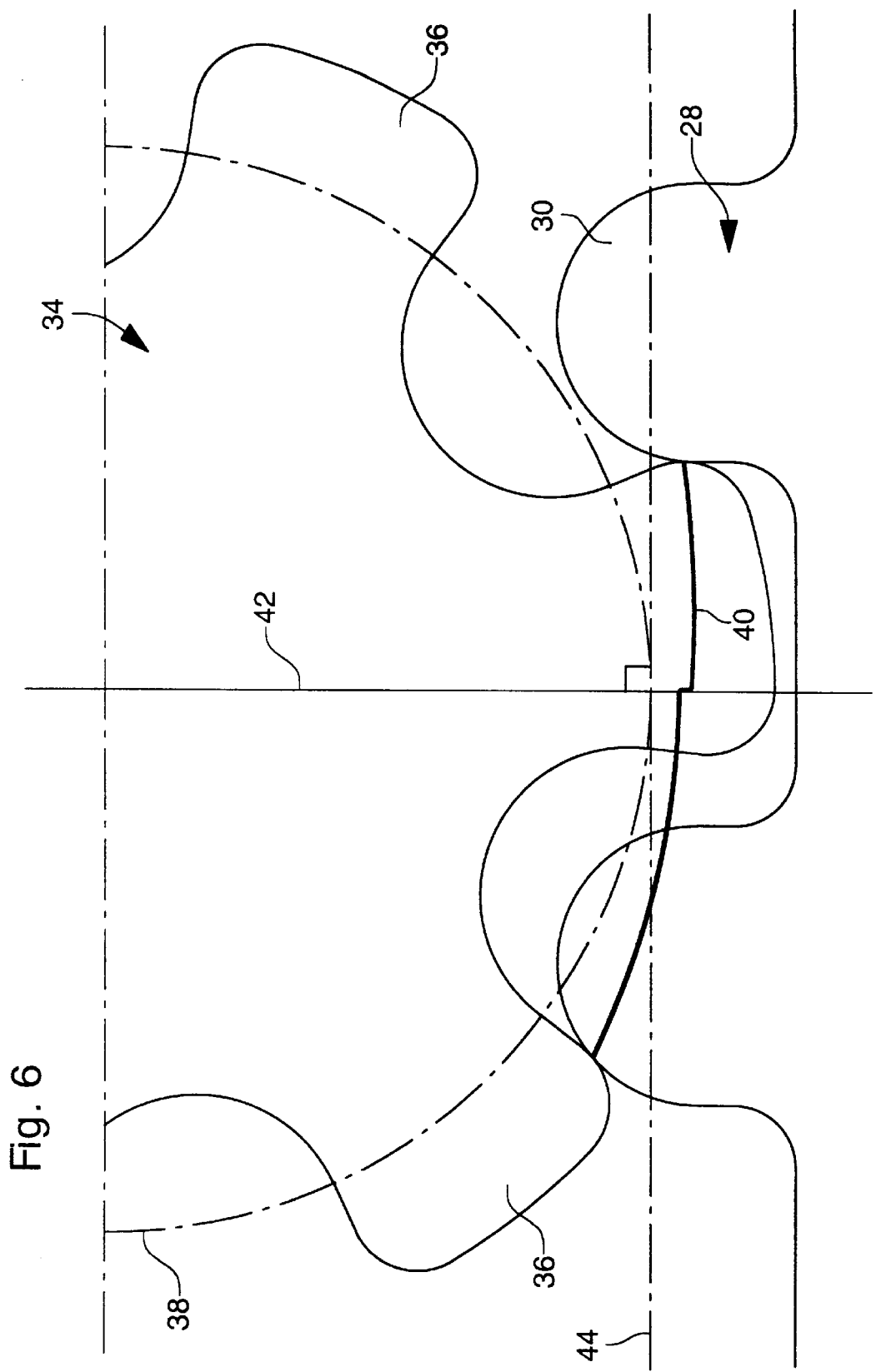
FIG. 6 is a partial view of the gearing system according to the invention.

The gearing system described hereinbefore is a system of special type having teeth of very high resistance. As FIG. 6 shows, the apparent number of teeth 36 of the driven pinion 34 of this system is at most six, distributed on the primitive diameter 38 of said driven pinion 34. According to an advantageous feature of the invention, the line 40 formed by the points of contact between the teeth 30 of the driver pinion 28 and the teeth 36 of the driven pinion 34 is longer after the neutral line 42 (output of the gearing) than before the neutral line 42 (input of the gearing). Neutral line 42 means herein the straight line that passes by the center of the pinion 34 and which is perpendicular to the straight line 44 tangential to the primitive diameter 38 of said pinion 34. This arrangement makes it possible to avoid any blockage point typical of standardized gearings with a small number of teeth for which the line of contact points is symetrical with respect to the neutral line. This creates a phenomenon of friction at the input of the gearing system.

According to another advantage of the invention, toothings 34 of jaws 8 each have an end of travel stop 46 which prevents axial sliding of cylindrical rack 28 in the fully open position of clamp 6. Rack 28 cannot therefore be lost, even in the event of breakage of transmission cable 2, or release of the weld or crimp connection by which control stem 26 is fixed to said transmission cable 2. The risk of seeing control stem 26 fall for example into a patient's organism is thus removed, which gives the present device a high level of security of use. It should also be noted that in the event of breakage of transmission cable 2, the closing of jaws 8 of clamp 6 nonetheless remains possible by simply pulling said clamp 6 back inside the endoscope tube, without risking damaging the latter.

A needle can also be provided at the end of cylindrical rack 28, so as to be able to place clamp 6 in a precise location prior to taking a sample by closing jaws 8.

It goes without saying that in addition to the means described, various simple modifications and variants fall within the scope of the present invention.

What is claimed is:

1. A device for taking samples, for example for biopsies, said device comprising a mechanical control system sliding inside a flexible sheath and connecting a control handle to a clamp formed of at least two pivoting jaws, wherein the control system includes a cylindrical rack having an annular tooth formed by an annular groove, and wherein the jaws of the clamp each have, on a circular portion of their perimeter, a toothing for engaging said annular tooth of the cylindrical rack for the opening and closing of said jaws.

2. A device for taking samples according to claim 1, wherein the toothing engages the cylindrical rack by at least two of its teeth.

3. A device for taking samples according to claim 1, wherein the apparent number of teeth distributed on the primitive diameter of the toothing is at most six.

4. A device for taking samples according to claim 1, wherein the cylindrical rack is formed by an alternating succession of annular teeth and annular grooves.

5. A device for taking samples according to claim 4, wherein the line formed by the points of contact between the teeth of the rack and the teeth of the toothing is longer after the neutral line than before said neutral line.

6. A device for taking samples according to claim 1, wherein the toothings of the jaws each have a stop which blocks the axial sliding of the cylindrical rack in an end of travel position.

7. A device for taking samples according to claim 1, further comprising a fork having a diametral groove in which a mounting portion of the jaws are housed.

8. A device for taking samples according to claim 1, wherein a needle is provided at the end of the cylindrical rack.

9. A device according to claim 1, wherein said cylindrical rack forms a driver pinion and said toothing forms a driven pinion to provide a gearing system.

10. A device according to claim 9, wherein the toothing engages the cylindrical rack by at least two of its teeth.

11. A device according to claim 9, wherein the apparent number of teeth distributed on the primitive diameter of the toothing is at most six.

12. A device according to claim 9, wherein the cylindrical rack is formed by an alternating succession of annular teeth and annular grooves.

13. A device according to claim 12, wherein the line formed by the points of contact between the teeth of the rack and the teeth of the toothing is longer after the neutral line than before said neutral line.

14. A device according to claim 9, wherein the toothings each have a stop which blocks the axial sliding of the cylindrical rack in an end of travel position.

* * * * *